(12) United States Patent
Hennink et al.

(10) Patent No.: US 6,303,300 B1
(45) Date of Patent: *Oct. 16, 2001

(54) POLY (ORGANO) PHOSPHAZENES FOR USE IN SYNTHETIC TRANSFECTION SYSTEMS

(75) Inventors: Wilhelmus Everhardus Hennink, Waddinxveen; Abraham Bout, Moerkapelle, both of (NL)

(73) Assignees: Introgen B.V.; Octoplus B.V.; Universiteit Utrecht, all of Heidelbereglaan (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/076,899

(22) Filed: May 13, 1998

Related U.S. Application Data (63) Continuation of application No. 08/817,912, filed as application No. PCT/NL96/00324 on Aug. 16, 1996, now Pat. No. 5,914,231.

(51) Int. Cl.[7] .............................. C12Q 1/70; C12N 1/63; C12N 15/85; C07H 21/04
(52) U.S. Cl. ........................ 435/6; 435/320.1; 435/455; 536/23.1
(58) Field of Search ................ 435/6, 172.3, 320.1, 435/455; 436/829; 536/23.1

(56) References Cited

U.S. PATENT DOCUMENTS

| | | | |
|---|---|---|---|
| 4,348,384 | 9/1982 | Horikoshi et al. | 424/450 |
| 4,900,556 | 2/1990 | Wheatley et al. | 424/450 |
| 5,004,611 | 4/1991 | Leigh | 424/450 |
| 5,529,777 | * 6/1996 | Andrianov et al. | 424/184.1 |

FOREIGN PATENT DOCUMENTS

WO95/35097 * 12/1995 (WO) .................... 424/489

OTHER PUBLICATIONS

Verma et al. Gene therapy–promises, problems and prospects. Nature vol. 389:239–242, Sep. 18, 1997.*
Editorial, Gene therapy: Better vectors, less hype. Nature Biotechnology. vol. 15:815, Sep. 15, 1997.*
Marshall, E. Gene therapy's growing pains, Science vol. 269:1050–1055, Aug. 25, 1995.*
Orkin et al. Report and recommendations of the panel to assess the NIH investment in research on gene therapy, Dec. 7, 1995.*

* cited by examiner

*Primary Examiner*—Robert A. Schwartzman
*Assistant Examiner*—William Sandals
(74) *Attorney, Agent, or Firm*—Morrison & Foerster LLP (57) ABSTRACT

Water soluble polymers or polymeric hydrogels are used to encapsulate antigen to form vaccines. The antigen is mixed with a polymer solution, microparticles are formed of the polymer and antigen, and, optionally, the polymer is crosslinked to form a stable microparticle. Preferred polymers are alginate and polyphospazenes, and mixtures thereof. Microparticles can be administered parenterally or mucosally. For oral delivery, the microparticles are preferably fifteen microns or less in diameter, and adhere to the mucosal lining of the gastointestinal tract, increasing uptake by the reticuloendothelium.

5 Claims, 3 Drawing Sheets

Polymer: Mw = 26 kDa, degree of substitution = 75 %

Figure 4:

Polymer: Mw = 26 kDa, degree of substitution = 75 %

Polymer: Mw = 600 kDa, degree of substitution 100 %,
substituents: N,N-dimethylethanol amine and PEGME 2/1 mol/mol

POLY (ORGANO) PHOSPHAZENES FOR USE IN SYNTHETIC TRANSFECTION SYSTEMS

This application is a continuation of U.S. Ser. No. 08/817,912 filed Jun. 30, 1997, now U.S. Pat. No. 5,914,231 which is a national stage filing of PCT/NL96/00324 filed Aug. 16, 1996, the contents of which are incorporated herein by reference.

The present invention relates to the field of synthetic transfection systems useful in the delivery of gene constructs or DNA fragments to cells, especially to cells in living organisms. More in particular, the invention relates to cationic polymers having broad possibilities to be modified or adapted in order to create a flexible DNA gene delivery system, which can be used in, e.g., gene therapy applications.

Gene therapy is seen as a promising method to correct hereditary defects or to treat life threatening diseases such as cancer and AIDS. In gene therapy, nucleic acid fragments or gene constructs are brought into target cells. These nucleic acid fragments or gene constructs are preferably incorporated in plasmids or other vectors.

If the reconstructed plasmids are applied to an organism per se, this generally leads to low expression of the introduced gene, if any. There are three main reasons for this low expression. First, the plasmids will hardly ever reach the cell population where they are intended to be incorporated, due to degradation and elimination processes. Second, if the plasmids do reach the target cells, they cannot simply pass the cellular membrane, because of the strongly polar nature and the size of the plasmids. Third, if a plasmid does invade a target cell, it normally will be enclosed in an endosome, which will convert into a lysosome. In the lysosome, the plasmid will be degraded so that the incorporated gene cannot be expressed.

For the above reasons, in gene therapy plasmids comprising a desired gene construct are transported to and delivered in the target cells by means of carrier systems.

In recent years, many efforts have been made in the research on potentially suitable transfection systems, both of viral and non-viral origin. These transfection systems should deliver the desired gene to the target cell and cause it to be expressed to a high degree.

Viral vectors are very suitable, because by nature adapted, to introduce plasmids in target cells and to avoid endosome disruption, the degradation of the plasmids in endosomes or the transition of endosomes into lysosomes. However, viral vectors have a number of pronounced disadvantages. Viral vectors are able to effect integration of the introduced gene in the chromosomal DNA of the target cell. The site where this integration is effected cannot (yet) be predicted or controlled, which involves the risk of destroying essential genes or activation of, e.g., oncogenes. In addition, it is at present very difficult to provide for viral vectors on a commercial scale. Moreover, viral vectors generally trigger the immune system of a living organism, which will lead to immuno responses against the transfection system when used in vivo. Finally, viral vectors inherently set limits to the size of the gene construct to be introduced in the target cell.

In order to overcome the intrinsic disadvantages of viral vectors, synthetic transfection systems should offer good perspectives.

In this light, a review article of Kabanov et al. in Bioconjugate Chemistry vol. 6, no. 1 (1995), 7–20 is mentioned. This review article describes in general terms the principle of delivery of genetic material onto cells employing soluble in terpolyelectrolyte complexes (IPEC's) of nucleic acids with linear polycations. It is indicated that various polycations have been used to produce IPEC's. As explicit examples polyvinyl pyrimidinium salts, polypeptides such as polylysine conjugates and lipopolylysines, and spermines are mentioned.

Explicit reference is made to research carried out by the group of E. Wagner, relating to gene delivery by means of plasmid-polylysine complexes (Curiel et al., Adenovirus Enhancement of Transferrin-Polylysine-Mediated Gene Delivery, Proc. Natl. Acad. Sci. 88 (1991) 8850–8854; Plank et al., Gene Transfer into Hepatocytes Using Asialloglycoprotein Receptor Mediated Endocytosis of DNA Complexed with an Artificial Tetra-Antennary Galactose Ligand Bioconj. Chem. 3 (1992) 533–539; Wagner et al., Influenza Virus Hemagglutin HA2 N-Terminal Fusogenic Peptides Augment Gene Transfer by Transferrin-Polylysine-DNA Compleses: Toward a Synthetic Virus-like Gene-Transfer Vehicle, Proc. Natl. Acad. Sci. 89 (1992) 7934–7938; and Curiel et al., Gene Transfer to Respiratory Epithelial Cells via the Receptor Mediated Endocytosis Pathway, Am. J. Respir. Cell Mol. Biol. 6 (1992) 247–252). The plasmid-polylysine complex investigated upon exposition to certain cell lines showed at least some expression of the gene. Further, it was found that the expression efficiency increased considerably due to the binding of transferrin to the plasmid-polylysine complex. Transferrin gives rise to close cell-complex contact; it binds the entire complex to the transferrin receptor of cells. Subsequently, at least part of the entire complex was found to be incorporated in the cell.

However, the transfection efficiency of these polylysine based transfection systems as well as other known synthetic transfection systems is much lower than the efficiency of the known viral vectors.

The aim of the present invention is to provide for an effective and efficient synthetic transfection or blocking system. Such a system should fulfil the following conditions. The synthetic carrier system used must be biocompatible and preferably biodegradable. In order to be able to bind and condense DNA, e.g. in the form of a plasmid, wherein a gene construct is incorporated, the carrier system should possess a positive charge at physiological pH.

It has now been found that such a system can be based on polyphosphazenes which are at least partially substituted with cationic substituents. More in particular, the invention relates to water soluble or water dispersible poly(organo)-phosphazene based transfection systems, wherein organic cationic moieties are attached to the polyphosphazene backbone.

The polyphosphazene polymer which forms the basis of the poly(organo)phospnazene systems of the present invention essentially comprises a backbone of $-[-P(R)_2=N-]_n-$ units, wherein $(R)_2$ represents two groups, which may or may not be the same, coupled to the phosphorous atom. A restricted number of other units may, however, be present.

It is already known from other technical fields that polyphosphazenes are biocompatible and biodegradable. Polyphosphazenes were studied in the art of biomedical and pharmaceutical applications. In this light, reference is made to, e.g., the PhD Thesis of J. Goedemoed titled "Polyphosphazene Drug Delivery Systems for Antitumor Treatment", University of Leiden (1990); to Crommen et al. Biodegradable Polymers I, Synthesis of Hydrolysis-Sensitive Poly (organo)phosphazenes, Biomaterials 11 (1992), 511–520; to Domb et al. in Polymer Advanced Technology vol. 3, no. 6 (1992) 279–292; to Calicetti et al. in Il Farmaco vol. 49, no. 1, (1994) 69–74; and Andriarov et al. in J. Control Release vol. 27, no. 1 (1983) 69–77. These other technical fields essentially relate to controlled and sustained release systems.

In order to be able to bind to and condense with plasmids, the poly(organo)phosphazene used must—at physiological pH—at least contain 5% cationic radicals or groups coupled to the phosphorous atom in the —[—P(R)$_2$=N—]$_n$— units. Preferably, at least 40% and more preferably 50% cationic groups are coupled to the phosphorous atoms. In these cases, the polyphosphazene is able to bind DNA electrostatically and condense therewith. Moreover, degradation and elimination of the DNA in the systemic environment is avoided. In addition, it appeared that such polyphosphazene-DNA complexes are taken up in the target cells in a considerably higher amount as compared with the plasmids per se.

Suitable cationic substituents are preferably derived from organic moieties possessing an amino group. Such moieties are positively charged at physiological pH. Examples of these organic moieties are amino $C_{1-10}$ alcohols, and amino $C_{1-10}$ alkoxy $C_{1-10}$ alcohols, as well as their secondary, tertiary and quaternary derivatives. Especially, tertiary amines are preferred.

Although it is important that the polymer is positively charged as a whole, it is essential that the phosporous atoms in the poly phosphazene backbone not entirely comprise cationic moieties. Polyphosphazenes which are entirely substituted with cationic substituents essentially do not give rise to expression of the transported gene constructs. More in particular, part of the phosphorous atoms, preferably at least 10%, should be coupled to other hydrophobic and hydrophilic moieties.

Especially good results are obtained when at least 10% of the substituents coupled to the phosphorous atoms in the polymer backbone are derived from essentially electrically neutral organic hydrophilic substituents such as glycerol, methoxy ethoxy ethanol and polyethylene glycol. A possible explanation for these advantageous results is that the plasmid will be less tightly bound to the polymer, so that it can dissociate easier in the target cell. Further, it is noted that PEG avoids recognition by macrophages.

Hydrophobic groups, such as benzyl alcohol and lauryl alcohol, probably assist in transfer of the membranes of target cells.

The polyphosphazene used in accordance with the present invention is of a cationic nature, and it is water soluble or water dispersible. More in particular, very good results are obtained if one of the substituents R in the formula —[—P(R)$_2$=N—]$_n$— is a cationic group while the other substituent R may represent in 5–100% of the occurrences a cationic moiety and in 95–0% of the occurences an anionic or neutral moiety.

The molecular weight of the polyphosphazene polymers used can be easily adjusted to the size of the plasmid to be transported. Normally, polyphosphazenes having a molecular weight of from 10,000 to 1,000,000 can suitably be used. The weight ratio of the polyphosphazene polymers to the DNA fragments is very critical. The transfection efficiency does increase with increasing polymer to plasmid ratios. Suitable results are obtained when using weight ratios of between 0.1 and 200, preferably this ratio is higher than 1 most preferably higher than 7. The length of the polyphosphazene polymers can be controlled by using and maintaining suitable reaction conditions in the polymerization process.

The synthetic transfection system of the invention which comprises at least one cationic, water soluble or water dispersible polyphosphazene as a carrier further comprises a DNA fragment such as a vector, a plasmid, a gene construct or an oligonucleotide. Oligonucleotides can be used as a blocking structure in cells.

It is noted that the condensed particles comprising the polyphosphazene and DNA fragments can be enclosed or incorporated in known drug delivery systems, e.g. in liposomes.

Genes to be incorporated into vectors or vehicles to be used in the synthetic transfection system are among others documented in McKusick, V. A. Mendelian inheritance in man, catalogs of autosomal dominant, autosomal recessive, and X-linked pheno-types. Eighth edition. John Hopkins University Press (1988).

Stanbury, J. B., Wyngaarden, J. B., Frederickson, D. S., Goldstein, J. L. and Brown, M. S. The metabolic basis of inherited disease. Fifth edition. McGraw-Hill (1983).

These genes include but are not limited to:

genes associated with diseases of the carbohydrate metabolism such as for:
fructose-1-phosphate aldolase
fructose-1,6-diphosphatase
glucose-6-phosphatase
lysosomal α-1,4-glucosidase
amylo-1,6-glucosidase
amylo-(1,4:1,6)-transglucosidase
muscular phosphorylase
liver phosphorylase
muscular phosphofructokinase
phosphorylase-b-kinase
galactose-1-phosphate uridyl transferase
galactokinase
all enzymes of the pyruvate dehydrogenase complex
pyruvate carboxylase
2-oxoglutarate glyoxylate carboligase
D-glycerate dehydrogenase;

genes associated with diseases of the amino acid metabolism such as for:
phenylalanine hydroxylase
dihydrobiopterin synthetase
tyrosine aminotransferase
tyrosinase
histidase
fumarylacetoacetase
glutathione synthetase
γ-glutamylcysteine synthetase
ornithine-δ-aminotransferase
carbamoylphosphate synthetase
ornithine carbamyltransferase
argininosuccinate synthetase
argininosuccinate lyase
arginase
L-lysine dehydrogenase
L-lysine ketoglutarate reductase
valine transaminase
leucine isoleucine transaminase
"branched chain" 2-keto acid decarboxylase
isovaleryl CoA dehydrogenase
acyl-CoA dehydrogenase
3-hydroxy-3-methylglutaryl CoA lyase acetoacetyl CoA 3-ketothiolase
propionyl CoA carboxylase
methylmalonyl CoA mutase
ATP:cobalamrine adenosyltransferase
dihydrofolate reductase
methylene tetrahydrofolate reductase
cystathionine β-synthase
sarcosine dehydrogenase complex
proteins belonging to the glycine cleavage system
β-alanine transaminase
serum carnosinase
cerebral homocarnosinase;
genes associated with diseases of fat and fatty acid metabolisms such as for:
lipoprotein lipase
apolipoprotein C-II
apolipoprotein E
other apolipoproteins
lecithin cholesterol acyltransferase
LDL receptor
liver sterol hydroxylase
"Phytanic acid" α-hydroxylase;
genes associated with lysosomal defects such as for:
lysosomal α-L-iduronidase
lysosomal iduronate sulphatase
lysosomal heparan N-sulphatase
lysosomal N-acetyl-α-D-glucosaminidase
lysosomal acetyl CoA: α-glucosaminide N-acetyltransferase
lysosomal N-acetyl-α-D-glucosaminide 6-sulphatase
lysosomal galactosamine 6-sulphate sulphatase
lysosomal β-galactosidase
lysosomal arylsulphatase B
lysosomal β-glucuronidase
N-acetylglucosaminylphosphotransferase
lysosomal α-D-mannosidase
lysosomal α-neuraminidase
lysosomal aspartylglycosaminidase
lysosomal α-L-fucosidase
lysosomal acid lipase
lysosomal acid ceramidase
lysosomal sphingomyelinase
lysosomal glucocerebrosidase
lysosomal galactosylceramidase
lysosomal arylsulphatase A
α-galactosidase A
lysosomal acid β-galactosidase
α-chain of the lysosomal hexosaminidase A;
genes associated with diseases of the steroid metabolism such as for:
21-hydroxylase
11β-hydroxylase
androgen receptor
steroid 5α-reductase
steroid suiphatase;
genes associated with diseases of the purine and pyrimidine metabolism such as for:
phosphoribosylpyrophosphate synthetase
hypoxanthine guanine phosphoribosyltransferase
adenine phosphoribosyltransferase
adenosine deaminase
purine nucleoside phosphorylase
AMP deaminase
xanthine oxidase
orotate phosphoribosyltransferase
orotidine 5'-phosphate decarboxylase
DNA repair enzymes;
genes associated with diseases of the porphirine and haemal metabolism such as for:
uroporphyrinogene III cosynthase
ferrochelatase
porphobilinogene deaminase
coproporphyrinogene oxidase
proporphyrinogene oxidase
uroporphyrinoqene III synthase
uroporphyrinogene decarboxylase
bilirubine UDP-glucuronyltransferase
catalase;
genes associated with diseases of the connective tissue, muscles and bone such as for:
lysyl hydroxylase
procollagen peptidase
α1-antitrypsine
dystrophine
alkaline phosphatase
guanosine nucleotide regulatory protein of the adenyl cyclase complex;
genes associated with diseases of the blood and blood-forming organs such as for:
blood coagulation factor V
blood coagulation factor VII
blood coagulation factor VIII
blood coagulation factor IX
blood coagulation factor X
blood coagulation factor XII
blood coagulation factor XIII
all other blood coagulation factors
all genes associated with osteopetrosis such as for: "carbonic anhydrase II"
thrombocytes membrane glycoprotein Ib
thrombocytes membrane glycoprotein IIb–IIIa
spectrin
pyruvate kinase
glucose-6-phosphate dehydrogenase
NADH cytochrome $b_5$ reductase
β-globin
α-globin;
genes associated with diseases of transport systems such as for:
lactase
sucrase-α-dextrinase
25-hydroxyvitamin $D_3$-1-hydroxylase
cystic fibrosis transmembrane conductance regulator (CFTR);
genes associated with congenital immunodeficiencies such as for:
the proteins of the complement system including B, C1q, C1r, C2, C3, C4, C5, C7, C8 and C10 the inhibitor of C1, a component of the complement system the inactivator of C3b, a component of the complement system;

the genes for X-bound immunodeficiencies such as for:

one of the enzymes of the NADPH oxidase complex myeloperoxidase the syndrome of Wiscott Aldrich and Ataxia Telangiectasia;

genes coding for hormones as well as the genes coding for their receptors such as for instance for:

growth hormone.

Further, these genes also include genes which (to date) have not been associated with a hereditary defect but with which gene therapy can be practised in some manner.

These include:

the gene for tyrosine hydroxylase;

drug resistance genes such as for instance:

the P-glycoprotein P170 (the so-called multi drug resistance gene mdr1)

mdr 3 dihydrofolate reduitase (DHFR) and methotrtxate resistant isotypes thereof metallothioneine aldehyde dehydrogenase (ALDH)

glutathione transferase;

genes coding for all cytokins including for instance all interleukins and all interferons;

genes coding for all growth factors;

genes coding for all growth factor receptors;

genes coding for all transplantation antigens such as for instance the major and minor histocompatibility antigens;

genes capable of affording resistance against infectious organisms, such as for instance TAR decoys;

genes of infectious organisms which can be used for vaccination purposes such as for instance the envelope gene of HIV;

genes which can be used for negative selection such as for instance the thymidine kinase gene of the Herpes simplex virus against which selection can be effected with substrates such as for instance gancyclovir or acyclovir.

Vectors to be used include viral and non-viral regulatory elements for expression and/or replication. These vectors are well known in the field.

Suitable transfection systems are able to target a gene construct to the aimed cell population. The polyphosphazene based transfection system of the invention therefore at least comprises one group that is selectively targetted to target molecules associated with the surfuace of the target cells. Such targeting moieties or homing devices are known to the skilled person and comprise, e.g., tri and tetra antennary cluster glycosides, transferrin or other protein contructs, monoclonal antibodies against cell membrane proteins, ligands for cell surface associated receptors and binding fragments of derivatives of said targeting moieties etc. If, for instance, galactose moieties are coupled to the polyphosphazene system of the present invention the transported gene fragments are incorporated in hepatocytes through the galactose receptor of hepatocytes. Furthermore, the presence of recognizable structures covalently or non-covalently coupled to the polyphosphazene part of a polyphosphazene-DNA complex facilitates the incorporation of the gene construct in the target cell.

Moreover, the transfection system can be adapted to allow the gene construct to leave endosomes in the cellular system.

Thereto membrane destabilizing structures, in particular polypeptide fragments, are conjugated to the poly(organo) phosphazene systems. Such destabilizing structures should be able to disturb or destabilize the endosomal membrane systems. The plasmids incorporating a gene construct so reach the cytoplasm of the target cell, where the gene construct can be expressed. Examples of such membrane destabilizing structures which are suitably used in accordance with the present invention are fusogenic structures, e.g. certain peptides and (parts of) viral coating proteins, for instance peptides derived from hemagglutinin protein of the influenza virus (see in this respect, e.g., Plank et al. The Influence of Endosome-Disruptive Peptides on Gene Transfer Using Synthetic Virus-Like Gene Transfer Systems, J. Biol. Chem. 269 (1994), 12918–12924).

Another compound that is useful in accordance with the present invention is chloroquine. It is noted that chloroquine is only used in in vitro applications, because it is toxic in vivo. Since the invention is directed to both in vivo and in vitro applications, this embodiment is within the scope of the invention.

As said herein above polyphosphazenes are known per se. This also applies to methods of preparing these polymers. A preferred method to Drepare Dolvphosphazenes starts from hexachlorotriphosphazene. This starting compound is subjected to ring opening polymerization yielding poly dichlorophosphazene. Ring opening polymerization of hexachlorotriphosphazene in the bulk is for instance described in Kircheldorf (ed.) Handbook of Polymer Synthesis Part B, Chapter 17, Phosphorous-Containing Polymers (1991); while solution polymerization is described in Mujumdar et al. Solution Polymerization of Selected Polyphosphazenes, Macromol. Chem. 19, (1989) 2293–2302. Poly(organo) phosphazenes used in accordance with the present invention can be prepared from these poly dichloro phosphazenes by effecting nucleophilic substitution with organic compounds which are cationic at physiological pH or can easily be converted to such cationic substituents.

Random copolymers can be synthesized by carrying out the substitution reaction in the simultaneous presence of two or more substituents. It is also possible to subject the starting polymer first to a reaction with a first substituent and subsequently with another substituent. Suitable methods of these nucleophilic substitutions are well within the scope of the person skilled in the art.

Fusogenic peptides and targeting molecules can be bonded to the poly(organo)phosphazenes using well-known techniques, for instance using thiol groups introduced in the polymer and maleimide groups introduced in the peptide or targeting molecule.

In a preferred embodiment, the polyphosphazene polymer is substituted with N,N-dimethylamino ethanol groups. These cationic groups are introduced by contacting polydichloro-phosphazenes with N,N-dimethylamino ethanol.

In a further embodiment, the invention relates to a method for introducing DNA fragments in target cells, comprising contacting these DNA fragments with a polyphosphazene which is at least partially substituted with cationic substituents and subsequently contacting the obtained transfection system with target cells.

Finally, the invention relates to the use of a polyphosphazene which is at least partially substituted with cationic substituents as transfection vehicle.

The polyphosphazene system can be used both in in vivo and in in vitro applications.

The present invention will be described in further detail while referring to the following examples.

EXAMPLE 1

Water-soluble poly(organophosphazenes) with cationic side groups were synthesized as follows. Cyclic phosphazene trimer (hexachlorotriphosphazene) was polymerized to poly(dichloro)phosphazene by a solution polymerization using the method described by Mujumdar et al. (Macromolecules 1990 23, 14–21).

In a round bottom flask equipped with a condenser, hexachlorotriphosphaze (12 g; Aldrich, Belgium) was dissolved in 1,2,4-trichlorobenzene (10 ml, Aldrich, Belgium). Catalyst (sulfamic acid. 50 mg) and promotor ($CaSO_4.2H_2O$, 25 mg) were added. The reaction mixture was heated to 214° C. while stirring using a magnetic stirrer. The reaction was carried out under a nitrogen atmosphere. After a reaction time of 1 hour and 25 minutes, the reaction mixture was cooled to room temperature. Anhydrous hexane (20 ml) was added to precipitate the polymer and to extract unreacted monomer and low molecular weight products. The hexane phase was removed and the polymer was dissolved in about 50 ml anhydrous THF.

In a separate reaction, the sodium salt of N,N-dimethylethanolamine was prepared. To a solution of N,N-dimethylethanolamine (17 ml) in anhydrous THF (250 ml) in a three-neck round bottom flask equipped with a condensor. Na spheres (diameter 3–8 mm, 5 g) were added. This mixture was refluxed four 24 hours. After cooling to room temperature an additional 500 ml of THF was added, followed by the addition of the solution of poly (dichlorophosphazene) in THF (see above). After a reaction time of 7 days at room temperature, THF was evaporated under reduced pressure. The polymer was dissolved in about 250 ml water and extensively dialyzed against RO (reverse osmosis) water. The polymer was collected by lyophilization (yield 1–2 g). The degree of substitution was established by $^1$H-NMR, $^{31}$P NMR and titration experiments and amounted to 60%. It is assumed that the unsubstituted P—Cl groups (still present in the polymer after the reaction of poly (dichlorophosphazene) with the sodium salt of dimethylethanolamine) are converted into POH groups after contact with water. The weight average molecular weight (Mw) and number average molecular weight (Mn) relative to dextran were 52.000 g/mol and 19.000 g/mol respectively (GPC analysis, eluens: 0.8 M $NaNO_3$ in water).

A simular rection wherein the poly(dichlorophosphazene) was reacted under refluxing with the sodium salt of dimethylethanolamine for 7 days resulted in a polyer with a Mw=26.000 g/mol and Mn=12.500 g/mol; the degree of substitution amounted to 75%.

Figure 1:
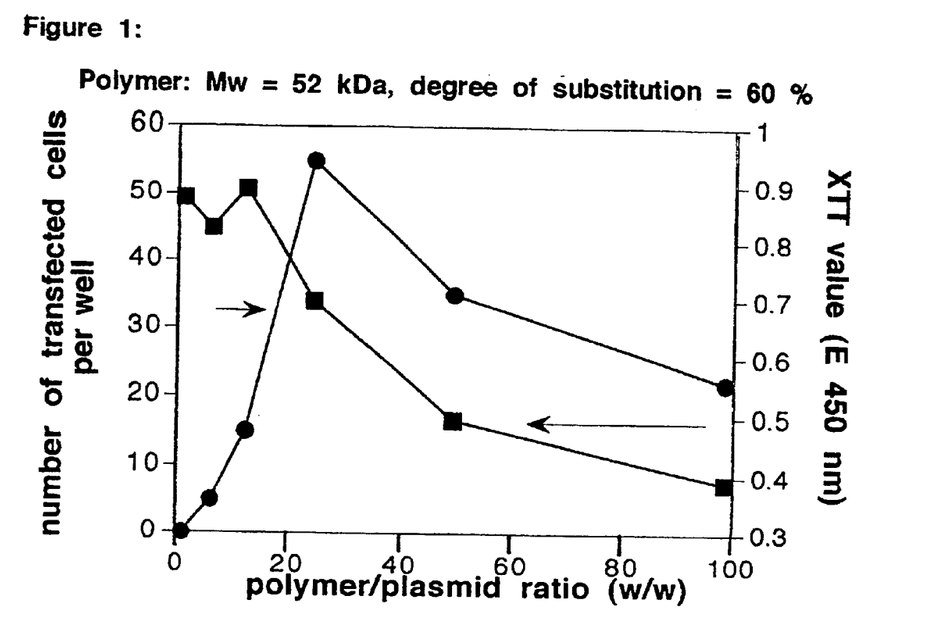
FIG. 1 shows the number of transfected COS-7 cells and the relative cell viability dependent on the polymer/plasmid ratio.
Figure 2:
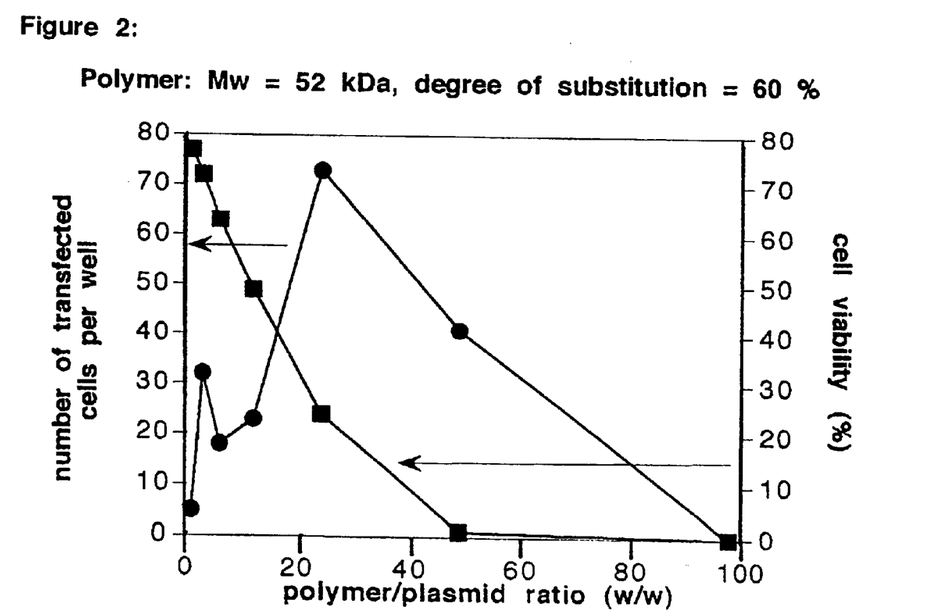
FIG. 2 shows the number of transfected OVCAR cells and the relative cell viability dependent on the polymer/plasmid ratio.
Figure 3:
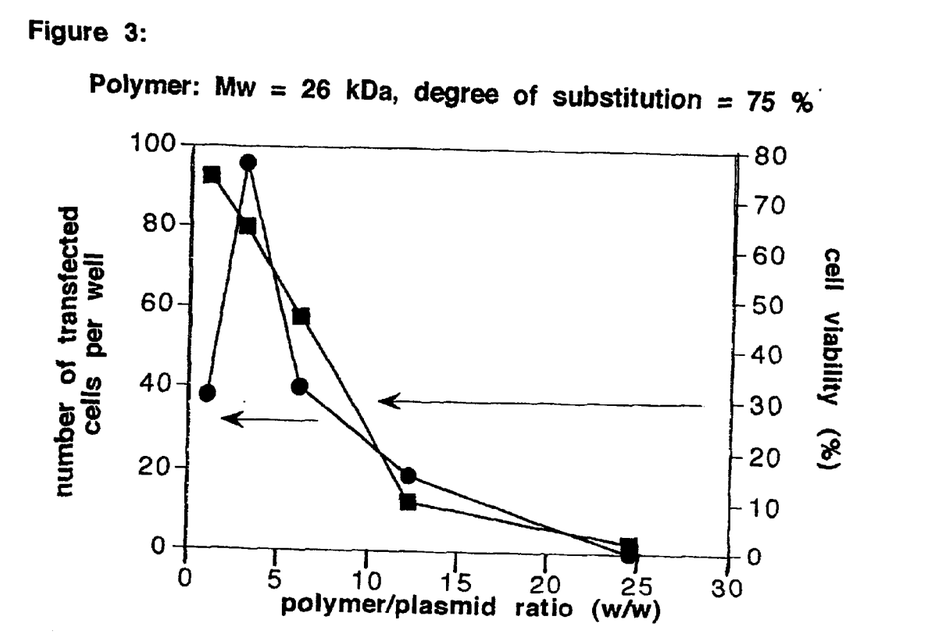
FIG. 3 shows the number of transfected OVCAR cells and the relative cell viability dependent on the polymer/plasmid ratio.

The transfection efficiency of polymer/plasmid complexes was evaluated in COS-7 and/or OVCAR 3-cells according to the protocol as described by J. Y. Cherng et al. (Pharm. Res. In press), PCMV-lacZ plasmid (7.8 kB) containing a bacterial lacZ gene preceded by a Nuclear Location Signal under control of the CMV promoter (A. Bout et al. Exp. Lung Res. 19 193–202, (1993) was used as reported gene. The polymer/plasmid complexes were prepared by adding 400 µl of cationic polyphosphazene (varying concentration too 100 µl of plasmid (final concentration 5 µg/ml). Both the plasmid and the polymer were dissolved in RPMI. This mixture was incubated for 1 hour at room temperature. The number of transfected cells was established by counting the number of blue spots in a well. The relative cell viability was determined using the XTT assay (D A Scudiero et al., Cancer Res. 48, 4827–4833, 1988). FIG. 1–3 shows the results.

Dynamic light scattering experiments showed that at a polymer/plasmid ratio >15 (w/w), particles with a hydrodynamic diameter of 200–300 nm were formed. At lower polymer/plasmid ratios, substantially larger particles (1000 nm) were formed. The polymer used had a Mw of 52.000 g/mol and a degree of substitution of 60%.

Figure 4:
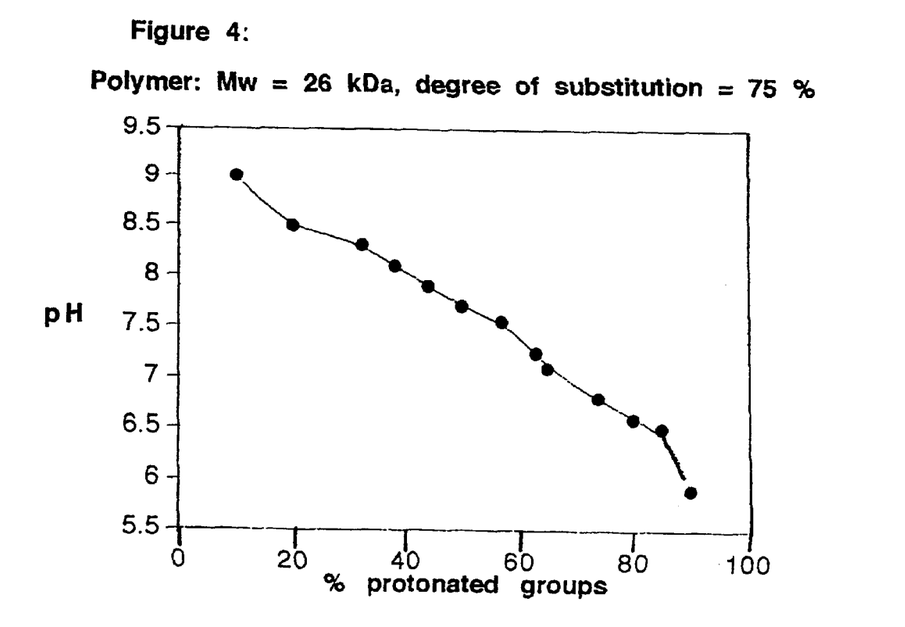
FIG. 4 shows the percentage of protonated amine side chains as function of the pH.

The degree of protonation under physiological conditions (pH 7.2, 0.9% NaCl) was determined by potentiometric titration. FIG. 4 shows the results. from this figure is appears that at pH 7.2 about 65% of the amine side chains is protonated.

Figure 5:
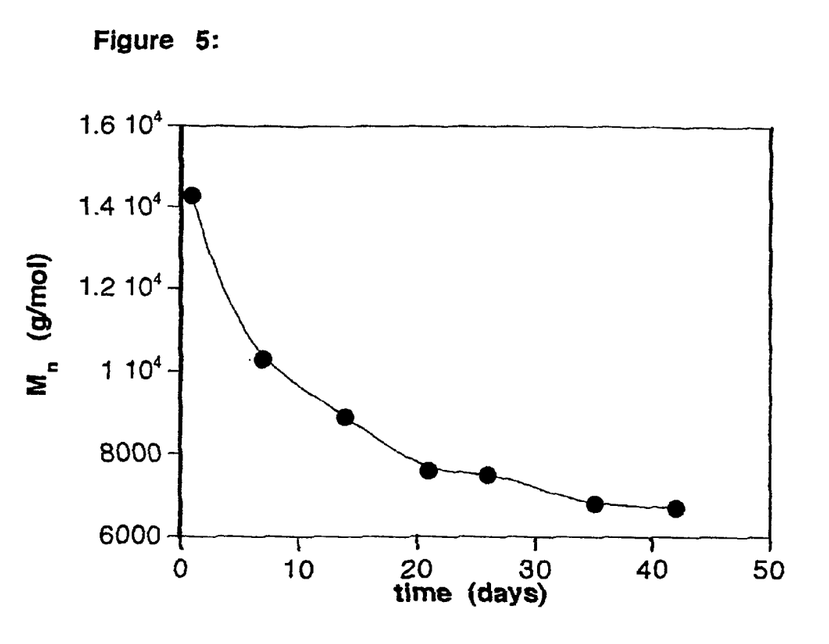
FIG. 5 shows the degradation of N,N-dimethyl-aminoalcohol substituted polyphosphazene (DS 75%) at 37° C., pH 7.2.

The degradation of polymer (Mw=26.000 g/mol, Mn=12.500) degree of substitution 75%) was studied. Therefore a solution of this polymer (26.1 mg) in 10 ml Hepes buffer (5 mM, pH 7.2) also containing 0.02% $NaN_3$ was incubated at 37° C. Periodically samples were withdrawn and analyzed by gel permeation chromatography (eluens 0.8 M $NaNO_3$). Molecular weights were determined relative to dextran. The results are shown in FIG. 5.

EXAMPLE 2

Figure 6:
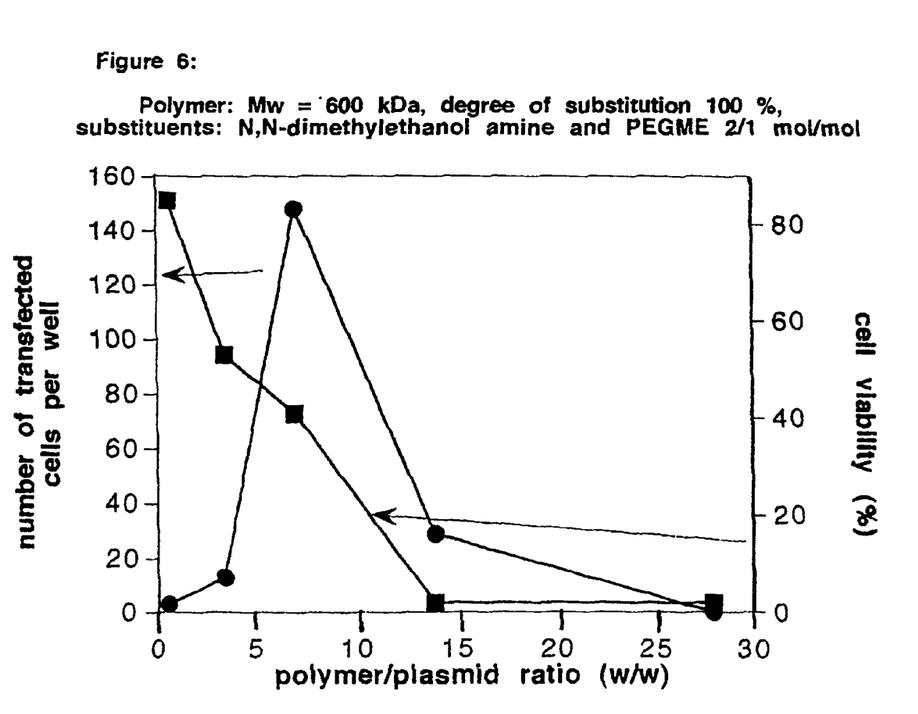
FIG. 6 shows the number of transfected OVCAR cells and the relative cell viability as a function of the polymer/plasmid ratio.

Poly(dichlorophosphazene) was synthesized essentially as described under example 1. Part of the Cl groups was substituted with N,N-dimethylethanolamine and part with PEGME (poly(ethyleneglycol)methylether), M=550 g/mol; Aldrich). This was carried out by refluxing a solution of poly(dichloro-phosphazene) and a mixture of the sodium salt of N,N-dimethylethanolamine (51 ml) and PEGME (40 ml) in THF (800 ml) for 4 days. The polymer was collected after dialysis and lyophilization as described under example 1. The molar ratio of N,N-dimethylethanolamine and PEGME as determined by $^1$H-NMR amounted to 2.Mw=600.000 g/mol, Mn=54.000 g/mol. The transfection efficiency of polymer/plasmid complexes was evaluated in OVCAR-3 cells (see example 1). The results are shown in FIG. 6.

The transfection efficiency of polymer/plasmid was also evaluated in 911 cells, described by Fallaux et al., Hum. Gene Ther. 7, 215–222, 1996.

The plasmid used for transfection was pCMV.lacZ (Bout et al., Exp. Lung. Res. 19, 193–202, 1993).

911 cells were cultured in Du Ibecco's Modified Essential Medium (DMEM) in the presence of 10% Fetal Bovine Serum (FBS). On day 0, $10^6$ 911 cells were seeded in 24 well plates (Nunc). On day 1, the culture medium was aspirated and DEEM (without FBS) containing different amounts of polymer/plasmid DNA was added to the cells in duplicate, in a volume of 500 µl. The ratios of polymer/plasmid (w/w) is indicated in the Table below. Per well of the 24 wells plate, 0.83 μg of pleasmid DNA was added. 1 hour after addition of the DMEM/polymer-plasmid to the cells, 500 μl of (DMEM+10% FBS) was added to the cells. After overnight incubation, the medium was replaced by 1 ml of DMEM+ 10% FBS. The cells were incubated for another 24 hours and then fixed and stained with X-GAL, as described in example 1. The percentage of X-GAL positive cells, recognizable by blue nuclei, was determined.

The results were as follows:

|  | % blue cells |
| --- | --- |
| co-polymer/plasmid ratio (w/w) | |
| 28:1 | 23 |
| 14:1 | 9 |
| 7:1 | 0.5 |
| 3:1 | <0.5 |
| homo-polymer/plasmid ratio (w/w) | |
| 28:1 | 20 |
| 14:1 | 7 |
| 7:1 | 3 |
| 3:1 | 0.5 |

The results indicate that a significant fraction of culture 911 cells can be transfected using polyorganophosphazenes. The transfection efficiency on 911 cells is increasing with increasing ratios of polymer to plasmid.

EXAMPLE 3

Poly(dichlorophosphazane) with varying molecular weights was synthesized essentially as described under example 1.

In a round bottom flask equipped with a condenser, hexachlorotriphosphaze (6 g) was dissolved in 1,2,4-trichlorbenzene (5 ml). Next, a varying amount of catalyst (sulfamic acid: 25, 100 a=or 350 mg) and a fixed amount of promoter ($CaSO_4 \cdot 2H_2O$, 25 mg) were added. The reaction mixture was heated to 214° C. under constant stirring using a magnetic stirrer in an inert atmosphere (dry nitrogen) for 75, 65 and 41 minutes respectively. The resulting polymers were precipitated in hexane, dissolved in anhydrous dioxane and subsequently added to a solution of the sodium salt of N,N-dimethylethanolamine (19 ml and 5 g Na spheres) in dioxane (600 ml). This reaction mixture was refluxed for 24 hours until no P—Cl groups (IR-analysis, 515 cm-1) could be detected. Thereafter a solution of the sodium salt of 2,2,2-trifluorethanol (3.2 ml and 1 g Na spheres) in dioxane (250 ml) was added to quench any residual P—Cl groups.

The polymers were isolated essentially as described under example 1. The next table gives the molecular weights (GPC analysis, relative to DEXTRAN).

| mg catalysis | MW (g/mol) | Mn (g/mol) |
| --- | --- | --- |
| 25 | 30500 | 11000 |
| 100 | 23600 | 9200 |
| 350 | 9700 | 4500 |

What is claimed is:

1. A synthetic transfection system comprising as a carrier a cationic, water-soluble or water-dispersible polyphosphazene and DNA to be transfected, wherein the DNA to be transfected is in the form of a plasmid, a vector, a gene construct or an oligonucleotide and wherein condensed particles comprising the polyphosphazene and DNA to be transfected are enclosed in a delivery vehicle, which is a liposome.

2. A synthetic transfection system comprising as a carrier a cationic, water-soluble or water-dispersible polyphosphazene and DNA to be transfected, wherein the polyphosphazene is coupled to a targeting moiety.

3. A method for introducing DNA into target cells which method comprises contacting target cells with a synthetic transfection system which comprises a polyphosphazene and said DNA, wherein the DNA to be transfected is in the form of a plasmid, a vector, a gene construct or an oligonucleotide wherein said synthetic transfection system comprises a liposome and wherein the DNA is introduced into said target cells.

4. A method for introducing DNA into target cells which method comprises contacting target cells with a synthetic transfection system which comprises a polyphosphazene and said DNA, wherein the polyphosphazene is coupled to a targeting moiety and wherein the DNA is introduced into said target cells.

5. The method of claim 4 wherein said targeting moiety is galactose or transferrin.

* * * * *

UNITED STATES PATENT AND TRADEMARK OFFICE
CERTIFICATE OF CORRECTION

PATENT NO. : 6,303,300 B1  
DATED : October 16, 2001  
INVENTOR(S) : Wilhelmus Everhardus Hennink et al.

It is certified that error appears in the above-identified patent and that said Letters Patent is hereby corrected as shown below:

<u>Title page,</u>
Item [73], Assignee, change "Introgen" to -- Introgene --

Signed and Sealed this

Twenty-third Day of July, 2002

Attest:

Attesting Officer

JAMES E. ROGAN
Director of the United States Patent and Trademark Office